United States Patent
Bandaru et al.

(10) Patent No.: US 10,537,303 B2
(45) Date of Patent: Jan. 21, 2020

(54) ULTRASOUND IMAGING SYSTEM AND METHOD FOR DETECTING POSITION AND ORIENTATION OF A COHERENT REFLECTOR

(71) Applicant: General Electric Company, Schenectady, NY (US)

(72) Inventors: Raja Sekhar Bandaru, Oslo (NO); Anders Sornes, Oslo (NO); Eigil Samset, Horten (NO); Jan D'Hooge, Mechelen (BE)

(73) Assignee: General Electric Company, Schenectady, NY (US)

( * ) Notice: Subject to any disclaimer, the term of this patent is extended or adjusted under 35 U.S.C. 154(b) by 1129 days.

(21) Appl. No.: 14/887,068

(22) Filed: Oct. 19, 2015

(65) Prior Publication Data

US 2017/0086781 A1   Mar. 30, 2017

Related U.S. Application Data

(60) Provisional application No. 62/233,740, filed on Sep. 28, 2015.

(51) Int. Cl.
*A61B 8/08* (2006.01)

(52) U.S. Cl.
CPC .................. *A61B 8/0841* (2013.01)

(58) Field of Classification Search
CPC .................................................. A61B 8/0841
See application file for complete search history.

(56) References Cited

U.S. PATENT DOCUMENTS

2004/0144176 A1*  7/2004  Yoden ................. A61B 8/0858
                                                          73/628
2007/0238954 A1*  10/2007  White ................... A61B 8/481
                                                          600/407

OTHER PUBLICATIONS

"GPU based real-time instrument tracking with three-dimensional ultrasound" by P.M. Novotny et al. Medical Image Analysis. 11 (2007) p. 458-464.*

* cited by examiner

*Primary Examiner* — Tse W Chen
*Assistant Examiner* — Jason M Ip

(57) ABSTRACT

A method and ultrasound imaging system for detecting a coherent reflector comprises acquiring ultrasound channel data from a volume with a probe including a 2D aperture, calculating a MRT from the ultrasound channel data, identifying a first angle of a projection of the coherent reflector in a plane parallel to the 2D aperture based on the MRT, detecting a line-shaped echo pattern in the ultrasound channel data, determining a second angle of the coherent reflector with respect to the 2D aperture, determining a position and an orientation of the coherent reflector based on the first angle and the second angle, enhancing a representation of the coherent reflector in an image generated based on the ultrasound channel data, and displaying the image on a display device after enhancing the representation of the coherent reflector.

20 Claims, 10 Drawing Sheets

Delay-and-sum beamforming

Delay-and-MRT beamforming

Filter-delay-and-MRT beamforming

ULTRASOUND IMAGING SYSTEM AND METHOD FOR DETECTING POSITION AND ORIENTATION OF A COHERENT REFLECTOR

FIELD OF THE INVENTION

This disclosure relates generally to an ultrasound imaging system and method for detecting a position and orientation of a coherent reflector using ultrasound channel data.

BACKGROUND OF THE INVENTION

It is desirable to use ultrasound imaging to detect and track interventional devices such as catheters, guide wires, biopsy needles and other devices. Conventional techniques rely on data from other modalities, such as x-ray imaging, to detect the position of the interventional devices. Fluoroscopy, a form of x-ray imaging, provides accurate positional information regarding the interventional device, but it exposes both the patient and the clinician to ionizing radiation. Long-term exposure to ionizing radiation is known to be strongly correlated with negative health effects. Additionally, x-ray imaging is not well-suited for imaging soft tissue, and the knowledge about the precise position of various soft tissue structures is important information for the clinician to have during many interventional procedures. As such, clinicians either have to rely solely on the fluoroscopic images, which may lack vital information about soft tissue structures, or they may need to rely on multiple different imaging modalities. Using multiple imaging modalities either requires specific software to fuse the images together, or the clinician must mentally perform the fusion. In any type of image fusion, there is always the risk that the images may be misregistered, leading to a less precise, or even an ultimately unsuccessful, interventional procedure.

Ultrasound imaging is a non-ionizing modality that excels at imaging soft tissue. Conventional ultrasound techniques are not well-suited for imaging interventional devices, which are typically coherent reflectors. Ultrasound beamforming techniques typically assume that received acoustic reflections come from diffuse scatterers that reflect ultrasound energy in substantially all directions. This assumption proves useful and effective when imaging soft tissue in a patient. However, the underlying physics for coherent reflectors is significantly different than for diffuse scatterers. A coherent reflection is a mirror-like reflection obtained from insonifying a hard level surface with ultrasonic energy. Coherent reflections are common when imaging hard or metal objects, such as catheters and biopsy needles. Ultrasound echoes reflected from a coherent reflector behave according to Snell's law, which means that the angle of incidence is equal to the angle to reflection. Instead of reflecting ultrasound energy in substantially all directions, as is the case with a diffuse reflection, coherent reflections are typically very strong at positions where an angle of reflection of the reflected beam is equal to an angle of incidence. Specular reflections typically generate very little signal at most other locations. As such, ultrasound imaging systems only receive a signal from a coherent reflector if the transducer array is positioned to receive the reflected echo. Many of the echoes reflected from a coherent reflector do not intersect with the transducer array and are therefore not useful for constructing an image of the coherent reflector.

It is desirable to use ultrasound imaging to detect and track the real-time position of coherent reflectors such as catheters, guide wires, needles and other interventional devices. Standard beamforming techniques assume that the reflectors behave as diffuse scatterers. As such, standard beamforming techniques typically sum signals from a plurality of channels in order to form an ultrasound image. While this approach has proven very effective for soft tissue and other circumstances where the imaged material behaves as a diffuse scatterer, it is ineffective when imaging coherent reflectors. The coherent reflector will not contribute significant signal to elements when the reflected beam is away from the probe. And, if a conventional beamforming technique is applied to ultrasound data including a coherent reflection, the contributions of the coherent reflector tend to get minimized during the summing process. Therefore, conventional beamforming techniques are not effective for imaging coherent reflectors.

Conventional systems may use an external tracking system, such as an electromagnetic tracking system or an optical tracking system, to determine the position and orientation of an interventional device in real-time. However, using an external tracking system adds additional expense and complexity to the entire system. Additionally, the ultrasound system is required to be configured to interface with the tracking system if data showing the location and/or the trajectory of the interventional device is to be displayed in real-time.

It is also known to use a needle guide that acts as a fixture keeping the probe in a constant relative position with respect to a needle being imaged. While this technique is effective for imaging needles, the needle guide combined with the probe and the needle is bulkier and potentially more difficult to maneuver than a stand-alone needle. Additionally, this technique does not work to track other types of interventional devices that are disposed completely within the patient. In ultrasound biopsy, the needle guide is typically used to guide the needle into the tissue so that the needle is orthogonal to the transmit beam. In a 2D B-mode scan it is difficult for the operator to determine if the tip of the needle is inside the image frame. Determining if the tip of the needle is inside the 2D image typically involves a fair deal of trial- and error by inserting and retracting the needle. Conventional techniques are currently not well-suited for determining if the needle tip is inside of the 2D image frame. Conventional techniques rely completely upon operator experience to ensure that the needle tip is visible within the 2D image frame. As such, it is desirable to have an automated method to adjust the position of the 2D image frame so that the tip is visible in the 2D image frame.

While performing an interventional procedure, it is often very important to know the position and orientation of the interventional device, such as a needle, a catheter, or any other type of interventional device both to achieve the desired clinical outcome and to avoid potentially damaging surrounding tissue. For these and other reasons an improved method and ultrasound imaging system detecting and tracking coherent reflectors, such as catheter, guidewires, and biopsy needles is desired.

BRIEF DESCRIPTION OF THE INVENTION

The above-mentioned shortcomings, disadvantages and problems are addressed herein which will be understood by reading and understanding the following specification.

In an embodiment, a method of detecting a coherent reflector with an ultrasound imaging system including a processor and a display device includes acquiring ultrasound channel data from a volume with a probe including a 2D aperture, calculating with the processor a Modified Radon Transform (MRT) from the ultrasound channel data. The method includes identifying with the processor a first angle within a plane parallel to the 2D aperture where the MRT is at least one of a maximum value or above a threshold value. The method includes detecting, with the processor, a position of a line-shaped echo pattern in the ultrasound channel data, where the line-shaped echo pattern is produced by a reflection from the coherent reflector. The method includes determining, with the processor, a second angle of the coherent reflector with respect to the transmit aperture based on the position of the line-shaped echo pattern, determining, with the processor, a position and an orientation of the coherent reflector based on the first angle and the second angle. The method includes enhancing a representation of the coherent reflector in an image generated from the ultrasound channel data based on the MRT and displaying the image including the enhanced representation of the coherent reflector.

In an embodiment, an ultrasound imaging system includes a probe with a 2D aperture, a display device, a receiver in electronic communication with the probe, and a processor in electronic communication with the receiver and the display device. The processor is configured to acquire ultrasound channel data from a volume with the probe, calculate a MRT from the ultrasound channel data, identify a first angle within a plane parallel to the 2D aperture where the MRT is at least one of a maximum value or above a threshold value, and detect a position of a line-shaped echo pattern in the ultrasound channel data, where the line-shaped echo pattern is produced by a reflection from the coherent reflector. The processor is configured to determine a second angle of the coherent reflector with respect to the transmit aperture based on the position of the line-shaped echo pattern, determine a position and an orientation of the coherent reflector based on the first angle and the second angle, enhance a representation of the coherent reflector in an image generated from the ultrasound channel data based on the MRT, and display on the display device, the image including the enhanced representation of the coherent reflector.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
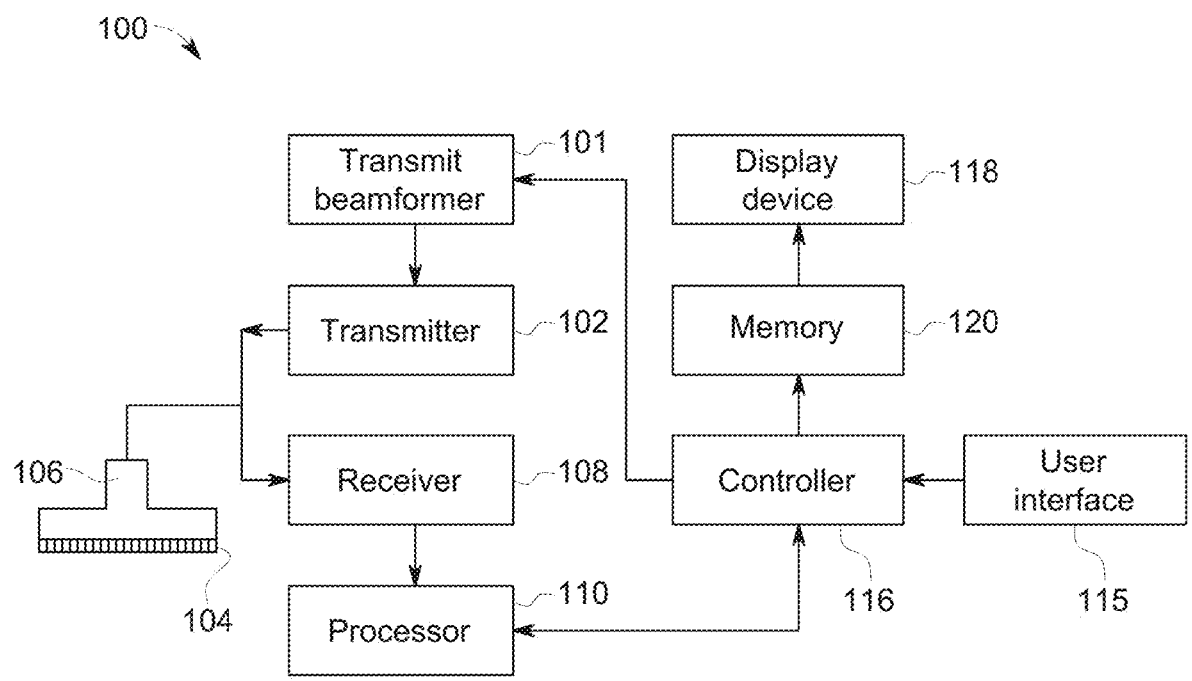
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a tissue (not shown). The probe 106 may be a 1.25 D array probe, a 1.5 D array probe, a 1.75 D array probe, or a 2D matrix array probe. The 2D matrix array probe may allow for full steering in both the azimuth and elevation directions. The pulsed ultrasonic signals are back-scattered from structures in the tissue, like blood cells or muscular tissue, to produce echoes that return to the elements 104. The echoes are converted into electrical signals, or ultrasound channel data, by the elements 104, and the electrical signals are received by a receiver 108. For purposes of this disclosure, the term "ultrasound channel data" will be defined to include ultrasound data from a plurality of different channels/elements prior to beamforming. Ultrasound channel data may therefore refer to data from either the probe 106 or the receiver 108. The processor 110 receives the ultrasound channel data from the receiver 108. The processor 110 may comprise one or more processors including any one or more of the following: a graphics processing unit (GPU), a microprocessor, a central processing unit (CPU), a digital signal processor (DSP), or any other type of processor capable of performing logical operations. The processor 110 may comprise a software beamformer, but it should be appreciated that the processor 110 may be separate from the software beamformer in other embodiments. As stated above, the processor 110 receives ultrasound channel data from the receiver 108. The processor 110 then applies the appropriate delays to the ultrasound channel data in order to focus on specific locations within a region or volume-of-interest.

The processor 110 may be adapted to perform one or more processing operations according to a plurality of selectable ultrasound modalities on the ultrasound channel data. The ultrasound channel data may be processed in real-time during a scanning session as the echo signals are received. For the purposes of this disclosure, the term "real-time" is defined to include a procedure that is performed without any intentional delay. For example, an embodiment may acquire and display data at a real-time frame-rate of 7-20 frames/second. However, it should be understood that the real-time frame rate may be dependent on the length of time that it takes to acquire each frame of data. Accordingly, when acquiring a relatively large region or volume of data, the real-time frame-rate may be slower. Thus, some embodiments may have real-time frame-rates that are considerably faster than 20 frames/second, while other embodiments may have real-time frame-rates slower than 7 frames/second. The data may be stored temporarily in a buffer (not shown) during a scanning session and processed in less than real-time in a live or off-line operation. Some embodiments of the invention may include multiple processors (not shown) and/or multi-core processors to handle the processing tasks assigned to processor 110 in the exemplary embodiment shown in FIG. 1.

According to other embodiments (not shown), the processor 110 shown in FIG. 1 may be replaced with two or more separate components. For example, an embodiment may include a processor and a separate software beamformer (not shown) that are both in parallel between the receiver 108 and a controller 116. According to this embodiment, both the processor and the software beamformer would receive ultrasound channel data from the receiver 108. The software beamformer would, for example, perform beamforming operations, and the processor would perform calculations related to the identification of coherent reflectors in the ultrasound channel data. According to an embodiment, the processor may calculate the position and orientation of the coherent reflectors in the data and transmit coordinates specifying the positions and/or orientations of any coherent reflectors to the controller 116. According to another embodiment, the software beamformer may generate an image based on the ultrasound channel data and the processor may produce a secondary image. The secondary image may, for instance, include information showing a graphical indicator of a coherent reflector. The controller 116 may display the secondary image as an overlay on top of the ultrasound image, or the secondary image may replace either some or all of the ultrasound image. Various ways of displaying information related to any coherent reflectors will be described hereinafter according to various embodiments.

According to some exemplary embodiments, the probe 106 may contain the components to do some or all of the transmit and/or the receive beamforming. For example, all or part of the transmit beamformer 101, the transmitter 102, the receiver 108 and the processor 110 may be situated within the probe 106. The terms "scan" or "scanning" may also be used in this disclosure to refer to acquiring data through the process of transmitting and receiving ultrasonic signals. Additionally, the terms "data" or "ultrasound channel data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like.

The ultrasound imaging system 100 also includes the controller 116 to control the transmit beamformer 101, the transmitter 102, and the receiver 108. The controller 116 may control the processor 110 according to some embodiments. According to other embodiments, the processor 110 may be a sub-component of the controller 116. According to other embodiments, the processor 110 may output images for display directly to the memory 120 or to the display device 118, instead of transmitting processed data to the controller 116 as shown in FIG. 1. Referring back to FIG. 1, the controller 116 is in electronic communication with the probe 106. The controller 116 may control the probe 106 to acquire data. The controller 116 controls which of the elements 104 are active and the shape of a beam emitted from the probe 106. According to some embodiments, the elements in the probe may be configured into a plurality of sub-apertures and the controller 116 may implement sub-aperture beamforming based on output from the sub-apertures. The controller 116 is also in electronic communication with a display device 118, and the controller 116 may process the ultrasound channel data into images for display on the display device 118. For purposes of this disclosure, the term "electronic communication" may be defined to include both wired and wireless connections. The controller 116 may include a central processor according to an embodiment. According to other embodiments, the controller 116 may include other electronic components capable of carrying out processing functions, such as a digital signal processor, a field-programmable gate array (FPGA) or a graphic board. According to other embodiments, the controller 116 may include multiple electronic components capable of carrying out processing functions.

The ultrasound imaging system 100 may continuously acquire ultrasound channel data at a frame-rate of, for example, 10 Hz to 30 Hz. Images generated from the ultrasound channel data may be refreshed at a similar frame-rate. Other embodiments may acquire and display ultrasound channel data at different rates. For example, some embodiments may acquire ultrasound channel data at a frame-rate of less than 10 Hz or greater than 30 Hz depending on the size of the region-of-interest and the intended application. A memory 120 is included for storing processed image frames for display at a subsequent time. Each image frame may include an associated time stamp indicating the time or relative time of acquisition to facilitate retrieval in the proper sequence from the memory 120. The memory 120 may comprise any known data storage medium.

In various embodiments of the present invention, ultrasound channel data may be processed by other or different mode-related modules by the processor 110 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

Figure 2:
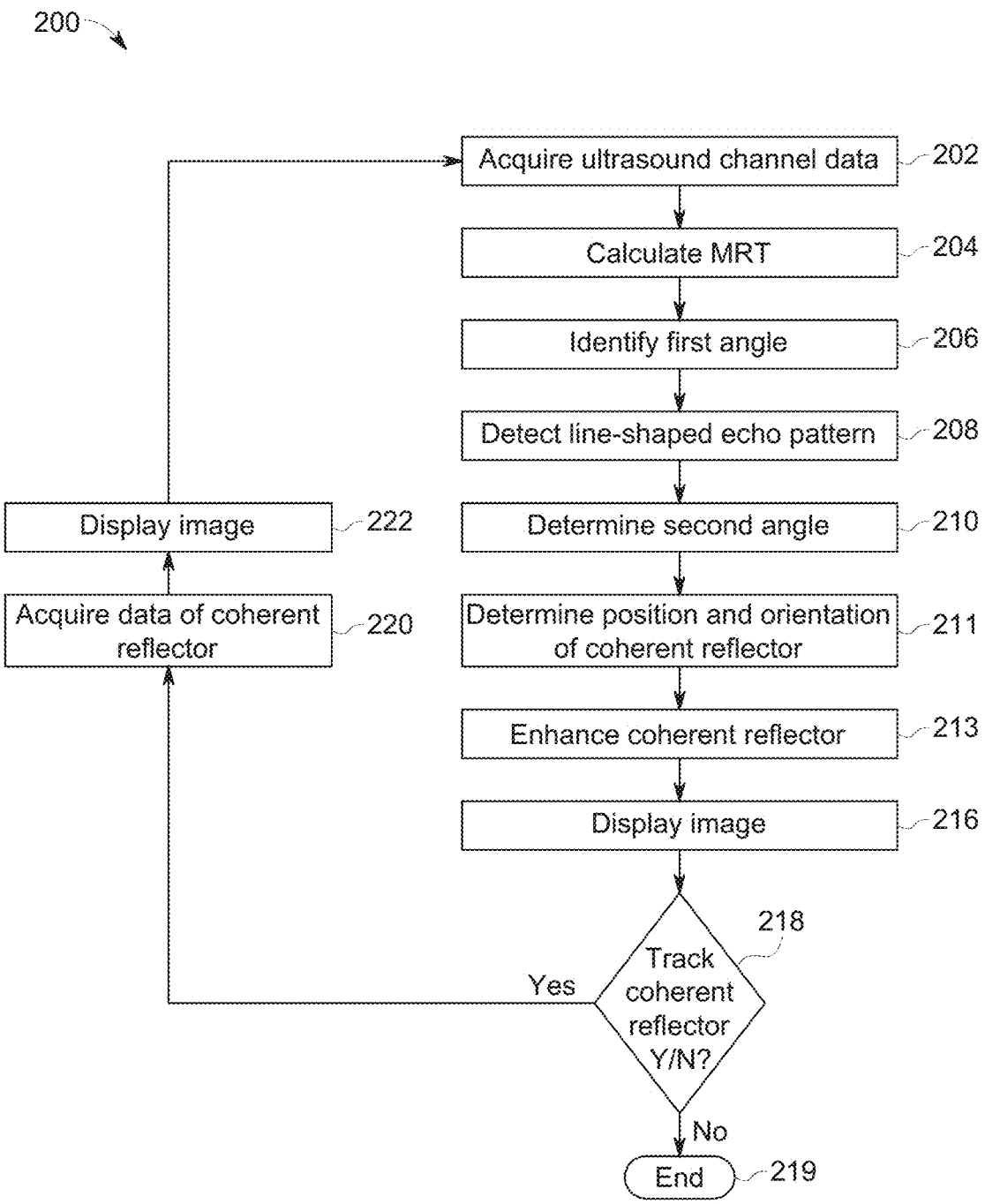
FIG. 2 is a flow chart of a method in accordance with an embodiment.

FIG. 2 is a flow chart of a method in accordance with an exemplary embodiment. The individual blocks of the flow chart represent steps that may be performed in accordance with the method 200. Additional embodiments may perform the steps shown in a different sequence, and/or additional embodiments may include additional steps not shown in FIG. 2. The technical effect of the method 200 is the display of an image with an enhanced representation of a coherent reflector.

Referring now to FIGS. 1 and 2, at step 202, the controller 116 controls the transmit beamformer 101, the transmitter 102, and the probe 106 to acquire ultrasound channel data. The probe includes a 2D aperture used for transmitting and receiving ultrasound energy. The ultrasound channel data may comprise 2D ultrasound channel data or 3D ultrasound channel data. Each channel may carry the data from one or more elements 104 in the probe 106. The ultrasound channel data may be acquired along a plurality of lines in a direction substantially perpendicular to the face of the probe 106 or some or all of the lines may be steered in either an azimuth or an elevation direction and are not necessarily perpendicular to the face of the probe 106. According to another embodiment, unfocused ultrasound energy may be used to acquire ultrasound channel data during step 202. For example, plane waves, spherical waves, or any other type of unfocused transmission schemes may be used to acquire the ultrasound channel data during step 202 in additional to various types of focused transmit beams. The controller 116 may, for instance, control the transmit beamformer 101 and the transmitter 102 to emit a transmit beam with a discrete focal point within the region or volume-of-interest. Next, the probe 106 receives reflected ultrasound signals from along each scan line. The receiver 108 receives unprocessed or raw ultrasound channel data from all of the elements 104 that are in the active receive aperture of the transducer array. The processor 110 may process the ultrasound channel data in order to generate pixel or voxel values at a plurality of different points representing different depths along each scan line. The processor 110 has access to the raw ultrasound channel data representing data from each channel. After receiving the raw ultrasound channel data, the processor 110, which may be a software beamformer according to an embodiment, may apply the appropriate delays to the ultrasound channel data in order to focus at specific depths along each scan line. The processor 110 may also emulate a conventional hardware beamformer and dynamically focus the receive beam as a function of depth along each scan line. The software beamformer may be configured to perform multi-line acquisition (MLA). For example, the processor 110 may acquire 2, 4, 6, 8, or 16 receive lines for each transmit line. It should be appreciated that the processor 110 may acquire a different number of receive lines for each transmit line according to other embodiments.

According to another acquisition scheme, the controller 116 may control the transmit beamformer 101 and the transmitter 102 to transmit two or more waves with different foci, so that each location within a field-of-view is insonified from at least two different directions. Therefore, at least two samples are acquired from multiple directions for each location in the field-of-view. The processor 110 may receive the ultrasound channel data from the probe 106 and apply retrospective transmit focusing (RTF) to the ultrasound channel data. When performing RTF, the processor 110 applies a time offset to at least one of the two or more samples acquired at each location. The processor 110 may then combine the samples after the offset has been applied. Applying the offset allows for the samples to be combined in-phase and the processor 110 can thus generate an image using the samples acquired based on two or more different transmit events, each with a different focus. According to another embodiment, the controller 116 may control the transmit beamformer 101 to emit unfocused ultrasound energy such as, for example, plane waves or spherical waves.

At step 204, the controller 116 calculates a Modified Radon Transform (MRT, hereinafter) based on the ultrasound channel data. It is known that a coherent reflector produces coherent echoes. This means that after the time delays have been applied, echoes from a coherent reflector will be of the same or nearly the same phase.

Many of the figures described hereinafter show an elongated coherent reflector. As a convention, this structure will be referred to as a "coherent reflector" when describing the following figures in this disclosure. However, it should be appreciated that the coherent reflector may be a biopsy needle, a catheter, or any other type of interventional device or anatomical structure that would act as a coherent reflector according to various embodiments.

Figure 3:
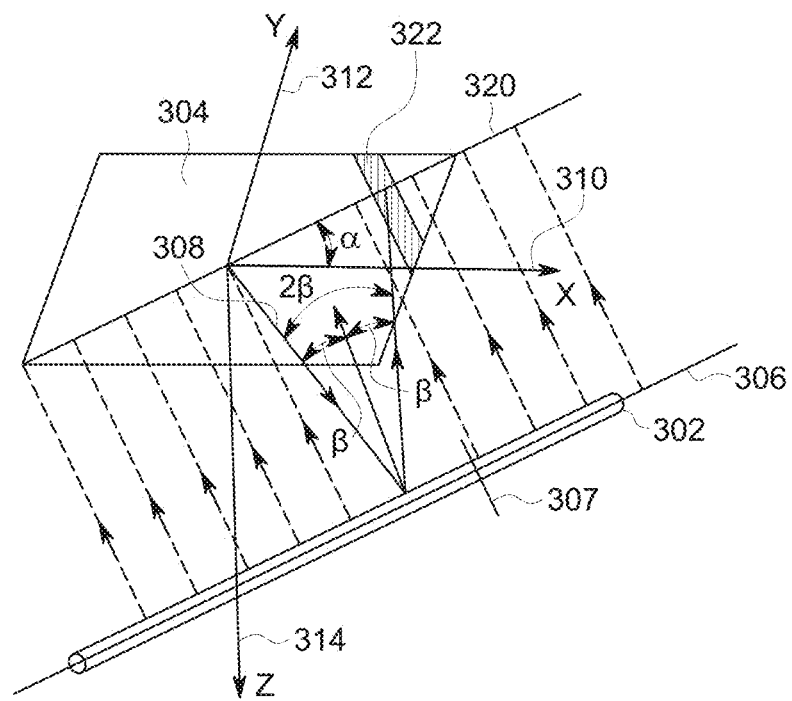
FIG. 3 is a schematic representation showing a coherent reflector with respect to a 2D aperture.

FIG. 3 is a schematic representation showing a coherent reflector 302 with respect to a 2D aperture 304. FIG. 3 includes a transmit beam 308. The transmit aperture 304 includes a x-direction 310, a y-direction 312, and a z-direction 314. A longitudinal axis 306 of the coherent reflector 302 is shown. FIG. 3 will be described in detail hereinafter.

Coherent reflectors with a generally circular cross-section, such as biopsy needles, catheters, etc., produce various echo patterns, or diffraction patterns, depending upon the orientation of the coherent reflector. For purposes of this disclosure, coherent reflectors will be described as having a long, or longitudinal axis, and a sectional axis, which is defined to be perpendicular to the longitudinal axis. For example, FIG. 3 shows the longitudinal axis 306 and a sectional axis 307.

Figure 4:
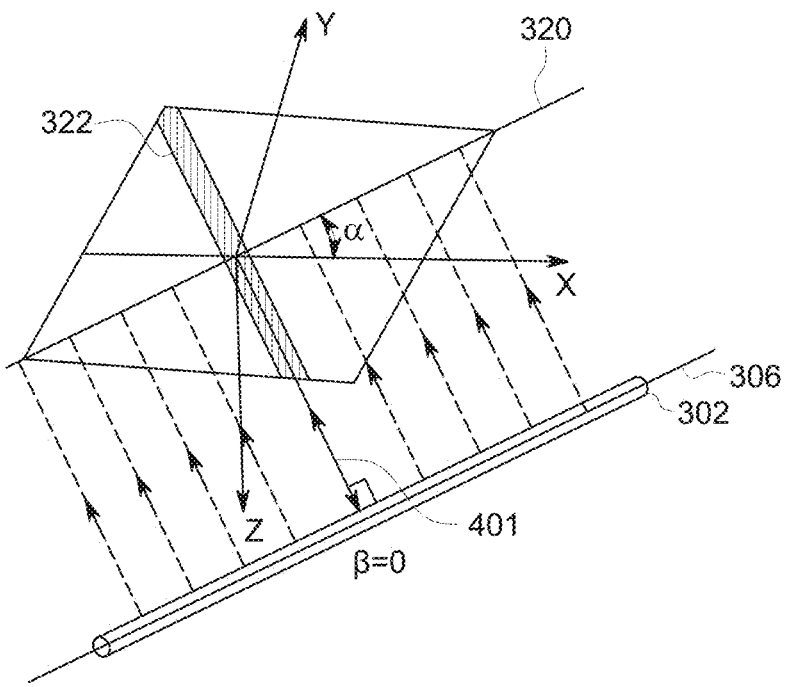
FIG. 4 is a schematic representation showing a coherent reflector with respect to a 2D aperture in accordance with an exemplary embodiment.
Figure 5:
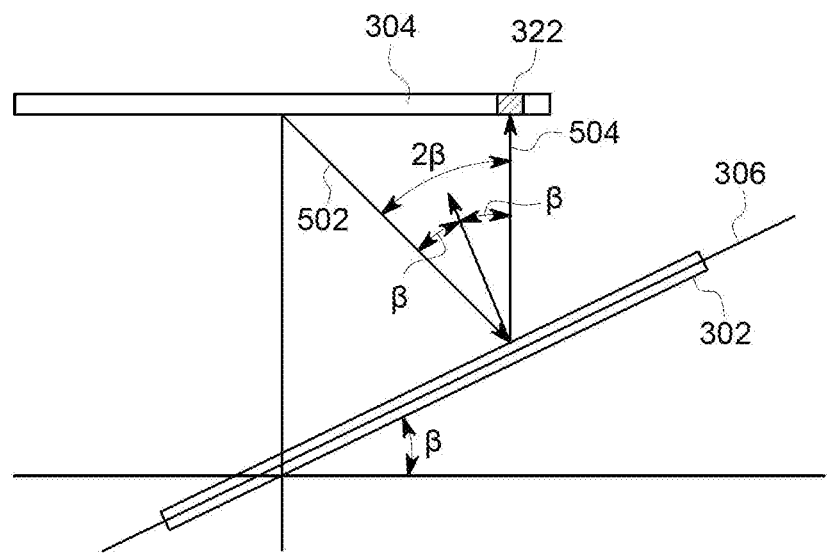
FIG. 5 is a schematic representation showing a 2D aperture with respect to a coherent reflector in accordance with an exemplary embodiment.
Figure 6:
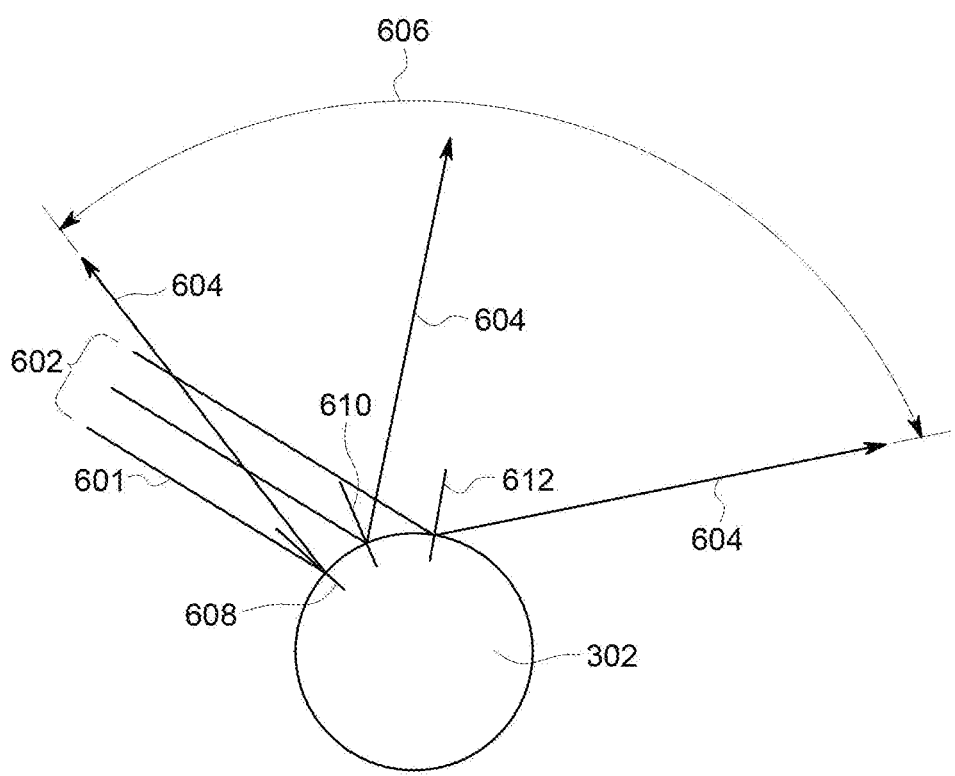
FIG. 6 is a schematic representation showing a reflection pattern in accordance with an exemplary embodiment.
Figure 7:
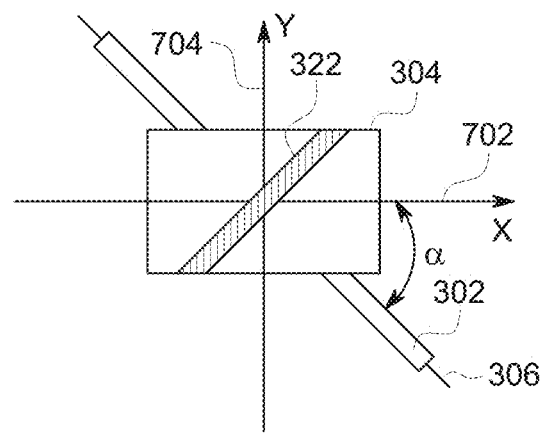
FIG. 7 is a "bird's eye" view showing a 2D aperture positioned with respect to a coherent reflector.

FIG. 4 is a schematic representation showing a diffraction pattern for a coherent reflector in accordance with an exemplary embodiment. The reflection is generated from a beam in a direction parallel to the longitudinal axis 306 of the coherent reflector 302. FIG. 5 is a schematic representation showing a 2D aperture with respect to a coherent reflector 302 in accordance with an exemplary embodiment. The reflection is based on a beam steered in a direction parallel to the longitudinal axis 306 in FIG. 5 as well. FIG. 6 is a schematic representation showing a diffraction pattern in accordance with an exemplary embodiment. In FIG. 6 the reflection is shown in the sectional direction that is perpendicular to the longitudinal axis. The longitudinal axis is in the direction into or out of the page and, as such, is not represented in FIG. 6. FIG. 7 is a schematic representation showing the 2D aperture 304 with respect to the coherent reflector 302 in accordance with an exemplary embodiment. FIG. 7 is a "bird's eye" view showing the 2D aperture 304 positioned over the coherent reflector 302. Common reference numbers will be used to describe identical structures in various figures.

FIG. 4 is a representation showing how an ultrasound beam 401 is reflected from the coherent reflector 302 in a direction parallel to the longitudinal axis 306. The ultrasound beam 401 behaves according to Snell's law where an angle of incidence $\Theta_i$ is equal to an angle of reflection $\Theta_r$, which are represented by $\beta$. In the example, both $\Theta_i$ and $\Theta_r$ are 90°. The ultrasound beam has an incident beam width 402 that is the same as a reflected beam width 404.

FIG. 5 is a representation showing how an incident line 502 of an ultrasound beam is reflected from the coherent reflector 302. The incident line 502 may be part of an transmit ultrasound beam. The orientation of the incident line 502 with respect to the coherent reflector 302 is different than that shown in FIG. 4. The surface normal of the coherent reflector 302 is disposed at an angle of β with respect to incident line 502. The reflected line 504 is reflected at an angle of 2*β with respect to the incident line 502 The reflected line 504 is detected by the 2D aperture 304 at a location 322.

FIG. 6 is a schematic representation showing how an incident ultrasound beam 601 is reflected by the coherent reflector 302 in a direction perpendicular to the longitudinal axis (not shown in FIG. 6). After reflecting from the coherent reflector 302 the ultrasound beam 601 diverges. The incident ultrasound beam 601 has an incident beam width 602, and the reflected ultrasound beam 604 has a reflected beam width 606 that is significantly wider than the incident beam width 602 due to the curved surface of the coherent reflector 302 in the direction perpendicular to the longitudinal axis. FIG. 6 includes a first normal line 608, a second normal line 610, and a third normal line 612. Each of the normal lines are shown normal, or perpendicular, to a surface of the coherent reflector 302 at the position where the respective normal line intersects the surface of the coherent reflector 302. The normal lines are disposed at different angles with respect to each other due to the curved surface. This, in turn, causes incident ultrasound beam 402 to diverge after being reflected from the coherent reflector 302. While the coherent reflector 302 shown in FIG. 6 has a circular cross-section, it should be appreciated that coherent reflectors may not be perfectly circular. As long as the surface of the coherent reflector is convex with respect to the incident ultrasound beam in a direction perpendicular to the longitudinal axis, the coherent reflector will produce a reflected beam that is wider than the incident beam in a manner consistent with that shown in FIG. 6. It should therefore be appreciated that other embodiments may be used to detect coherent reflectors with non-circular cross-sections. For example, other embodiments may be used to detect coherent reflectors with an oval or elliptical cross-sections.

FIG. 7 is a schematic representation showing how an incident ultrasound beam is reflected from the coherent reflector 302 in a direction perpendicular to the longitudinal axis 306 of the coherent reflector 302. The incident beam is not shown in FIG. 7, but it is directed at an origin of an x-axis 702 and a y-axis 704 in a direction perpendicular to the longitudinal axis 306. The 2D aperture 304 is represented in a position above the coherent reflector 302. A line-shaped echo pattern 322 represents the position where the reflected beam is detected by the 2D aperture 304

Figure 8:
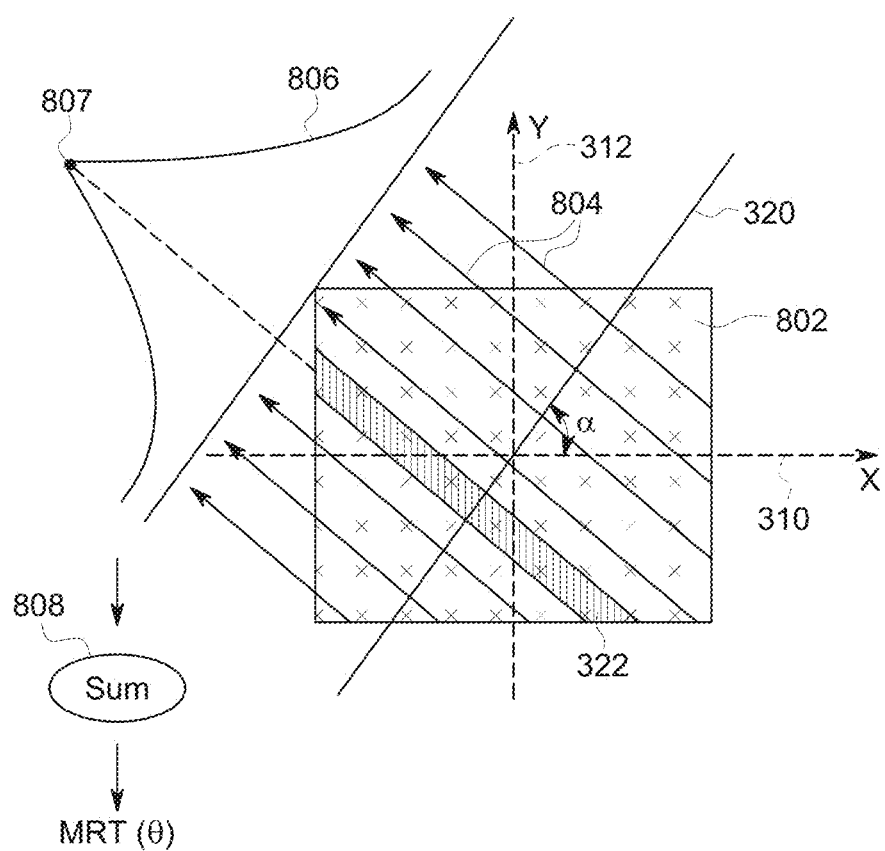
FIG. 8 is a schematic representation of how a Modified Radon Transform may be applied to ultrasound data according to an exemplary embodiment.

FIG. 8 is a schematic representation of how a Modified Radon Transform (MRT, hereinafter) may be applied to ultrasound data according to an exemplary embodiment. FIG. 8 includes a 2D aperture 802 with x's representing transducer elements. FIG. 8 includes the x-axis 310, the y-axis 312, the projection of the longitudinal axis of the coherent reflector 320, and the line-shaped echo pattern 322. The MRT is calculated for each individual angle Θ. The exemplary embodiment shown in FIG. 8 is calculated for an angle of approximately 45° from the y-axis. The angle Θ is represented by arrows 804. The values from the elements along vectors in the angle Θ are multiplied by each other to yield a value calculated along each vector. The values calculated along each vector are represented by line graph 806. Line graph 806 reaches a maximum value at a point 807 corresponding to the position of the line-shaped echo pattern 322 on the 2D aperture 802. After values have been calculated for all of the vectors, all the values are added together as represented by step 808. The MRT for the angle Θ represents the sum of the values from all the vectors disposed at the given angle Θ as expressed below in equations 1 and 2:

$$MRT(\theta, t) = \frac{1}{M*N} \sum_{\rho} \prod_{-M/2}^{\frac{M}{2}-1} \prod_{-N/2}^{\frac{N}{2}-1} v_d \cdot T \quad (1)$$

$$v_d = v(x, y, t - \tau_{m,n}) \text{ and } T = \delta(x\cos\theta + y\sin\theta - \rho) \quad (2)$$

where v is the instantaneous echo amplitude, $\tau_{m,n}$ is the delay, ρ is the sampling location in the direction of MRT calculation as shown in the figure, δ is the Dirac delta function to sample the grid in the direction of MRT, N&M are the number channels of the array.

Figure 9:
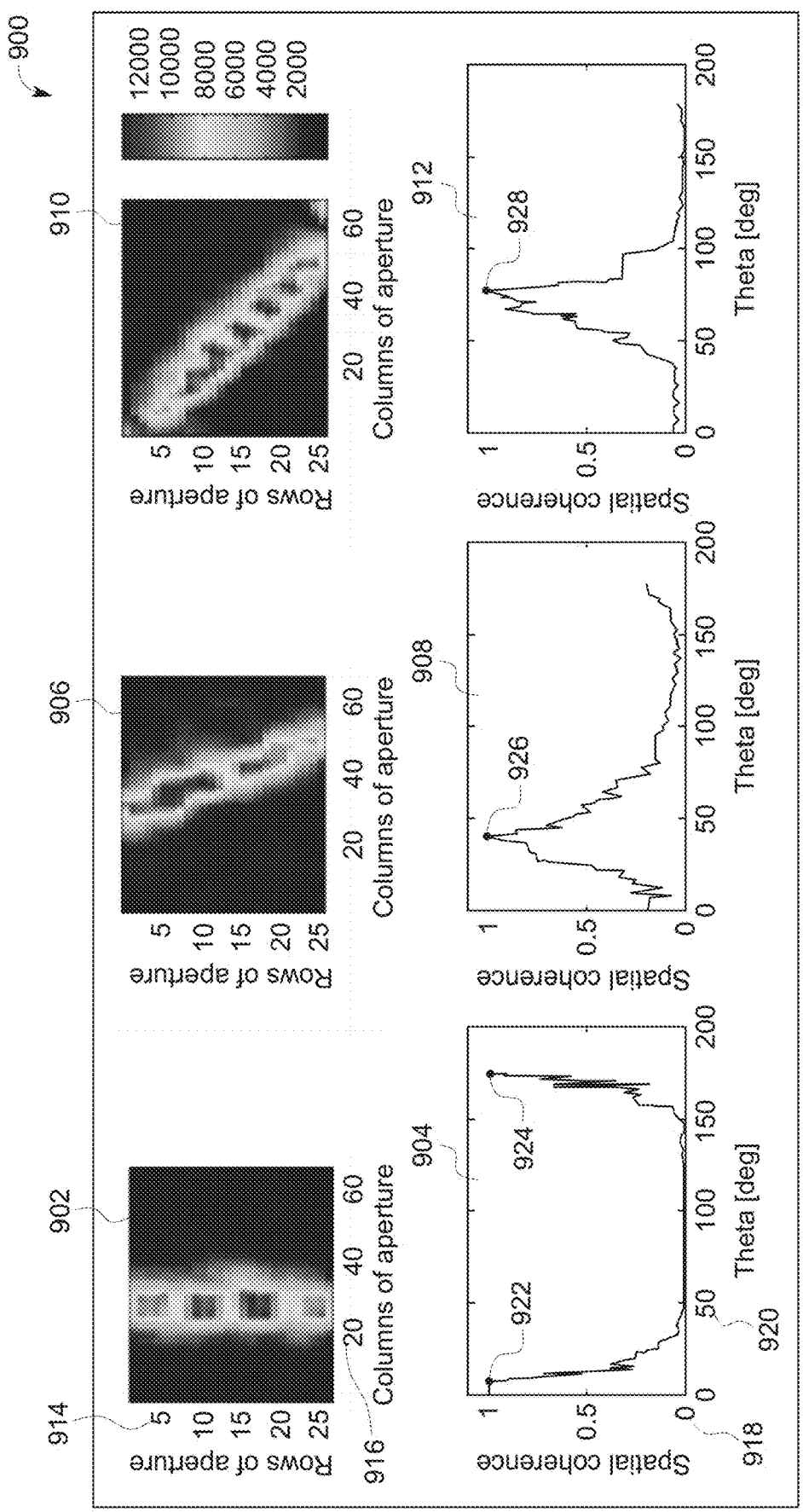
FIG. 9 is a representation showing an echo pattern and a corresponding MRT for three different orientations of a coherent reflector according to an exemplary embodiment.

FIG. 9 is a representation showing an echo pattern and a corresponding MRT for three different orientations of a coherent reflector according to an exemplary embodiment. A first echo pattern 902 and a first graph 904 are based on a coherent reflector disposed at an angle of 0° with respect to an x-direction 310 in the x-y plane. A second echo pattern 906 and a second graph 908 are based on a coherent reflector disposed at an angle of 40° with respect to the x-direction 310 in the x-y plane. A third echo pattern 910 and a third graph 912 are based on a coherent reflector disposed at an angle of 80° degrees with respect to the x-direction 31 in the x-y plane. The data reflected in FIG. 9 was acquired with a GE Vivid E95 using a 4V prove at 3 MHz on a Gammex 403GS.

A y-axis 914 represents rows of the 2D aperture while a x-axis 916 represents columns of the aperture. The first echo pattern 902 is a graphical representation of the amplitudes of a portion of the channel data. The second echo pattern 906 and the third echo pattern 910 are both also graphical representations showing rows of the aperture on a y-axis and columns of the aperture on an x-axis similar to the first echo pattern 902. The first graph 904 represents MRT along a y-axis and angle along an x-axis 920. The second graph 908 and the third graph 912 are both also representations showing MRT versus angle.

In the first graph 904, representing the MRT of ultrasound channel data acquired with the coherent reflector at 0 degrees, the peaks 922 and 924 of the MRT are shown at 0 degrees and at 180 degrees. In the second graph 908, representing the MRT of ultrasound channel data acquired with the coherent reflector disposed at 40 degrees, the peak 926 of the MRT is shown at approximately 40 degrees. In the third graph 912, representing the MRT of ultrasound channel data acquired with the coherent reflector at 80 degrees, a peak 928 of the MRT is shown at approximately 80 degrees.

These three examples of coherent reflectors at 0 degrees, 40 degrees, and 80 degrees show how the MRT may be used to identify an angle of the coherent reflector in the x-y plane. Calculating the MRT involves calculating a coherence at a plurality of discrete angles from 0 degrees to 180 degrees. According to an exemplary embodiment, calculating the MRT may involve calculating the MRT at 1 degree increments from 0 degrees to 180 degrees. However, it should be appreciated that other embodiments may perform the MRT calculations at different intervals. For example, some embodiments may calculate MRT at increments that are less than 1 degree, while others may calculate the MRT at intervals greater than 1 degree. However, it is desirable to calculate the MRT at a enough discrete angles so the controller 116 may determine an angle of maximum MRT.

Referring back to step 204 of the method 200 shown in FIG. 2, the controller 116 calculates the MRT from the ultrasound channel data. This includes calculating a MRT for a plurality of different angles based on the ultrasound channel data. As described above with respect to FIG. 8, the controller 116 may calculate the MRT for a plurality of different angle using the ultrasound channel data. The controller 116, may for instance calculate the MRT for every integral angle between 0 degrees and 180 degrees at 1 degree increments. According to other embodiments, the controller 116 may calculate the MRT at intervals that are either greater than 1 degree or less than 1 degree. According to preferred embodiments, the spacing between the adjacent angles, or samples, may be less than 10 degrees in order to obtain a resolution of less than 10 degrees when determining the orientation of the coherent reflector.

At step 206, the controller 116 identifies a first angle $\alpha$ of a projection of the coherent reflector onto a plane parallel to the 2D aperture, also referred to as the x-y plane. As previously discussed with respect to FIG. 6, the controller 116 may, for instance, identify an angle where the MRT is at a maximum in order to identify the first angle $\alpha$ (shown in FIG. 8). The first angle $\alpha$ represents the angle in the x-y plane from the x-axis. A line 320 is shown in the 2D aperture 304 that is used to illustrate the first angle $\alpha$. The line 320 is a projection of the coherent reflector 302 on the 2D aperture 304 (x-y plane). According to another embodiment, the controller 116, may identify either an angle or a range of angles that are above a predetermined threshold and then use either the angle or the range of angles to calculate the first angle $\alpha$.

At step 208, the controller 116 detects a line-shaped echo pattern 322 based on the ultrasound channel data. The line-shaped echo pattern 322 represents a reflection from the coherent reflector in a direction that is perpendicular to the longitudinal axis 306 as shown in FIGS. 3, 4, and 7.

At step 210 the controller 116 determines a second angle $\beta$ of the coherent reflector 302 with respect to the 2D aperture 304. FIG. 5 shows the coherent reflector 302 with respect to the 2D aperture 304. Controller 116 uses the position of the line-shaped echo pattern 322 to determine the second angle $\beta$ of the coherent reflector 302 with respect to the 2D aperture 304. The position of the line-shaped echo pattern 322 will shift in a direction parallel to line 320 due to the angle of the coherent reflector 302 with respect to the 2D aperture 304. The controller 116 starts with a known position of the incident line 502 from the transmit aperture 304 and a known focal position of the incident line 502. The controller 116 then detects the position of the line-shaped echo pattern and, based on the geometry of the transmit beam, the focal position, the line-shaped echo pattern 322, and the a priori knowledge that the angle of incidence equals the angle of reflection for a coherent reflector, the controller 116 calculates the angle of the coherent reflector that would result in the line-shaped echo pattern in the detected position. As shown in FIG. 5, the angle between the incident line 502 and the reflected beam 504 is 2*$\beta$. The second angle $\beta$ may be calculated based on the geometry shown in FIG. 5.

At step 211, the controller 116 uses the first angle $\alpha$ and the second angle $\beta$ to determine the position and orientation of the coherent reflector 302. The controller 116 uses the geometrical relationship between the transmit beams, focal points, the first angle $\alpha$ and the second angle $\beta$ to calculate the position and orientation of the coherent reflector 302.

At step 213, the controller 116 uses the position and orientation information of the coherent reflector 302 that was calculated at step 211 to enhance a representation of the coherent reflector. The controller 116 may enhance a representation of the coherent reflector in an image generated based on the ultrasound channel data. Enhancing the representation of the coherent reflector in the image may include generating a graphical indicator representing the coherent reflector and displaying the graphical indicator on the image. The graphical indicator may include a line, an arrow, a cylinder, or any other graphical object that may be used to represent the position and orientation of the coherent reflector. According to some embodiments, the graphical indicator may include highlighting the portion of the image representing the coherent reflector in a different color.

At step 216, the controller 116 displays the image, including the enhanced representation of the coherent reflector on the display device 118.

Figure 10:
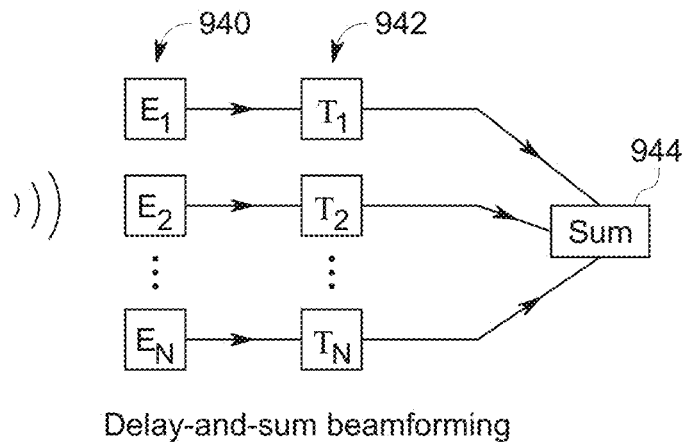
FIG. 10 is a schematic representation of a conventional delay-and-sum beamforming technique in accordance with an embodiment.

According to other embodiments, enhancing the representation of the coherent reflector may include modifying the beamforming using the MRT. A conventional delay-and-sum beamforming technique is shown below in equation 3:

$$s(t) = \frac{1}{N} \sum_{n=1, m=1}^{N,M} v(t - \tau_{n,m}) \quad (3)$$

where s is the sum, v is the instantaneous echo amplitude, $\tau_{n,m}$ is the delay correction applied, N and M are the number of channels of the array. FIG. 10 is a schematic representation of a conventional delay-and-sum beamforming technique. FIG. 10 includes a first column 940, with elements number $E_1, E_2, \ldots, E_N$, where N represents the total number of elements. A second column 942 represents the delays applied to the ultrasound data from each of the elements. The delays are represented as $T_1, T_2, \ldots, T_N$. At 944, all of the signals are summed together after the appropriate delays have been applied. The standard delay-and-sum approach therefore sums data from all of the elements acquired at a specific depth.

However, instead of using delay-and-sum beamforming, according to an embodiment, the controller 116 may use the values of the MRT at the angle where the MRT is at a maximum for each location. The MRT function is shown below in equation 2:

$$d(t) = \text{MRT}(\theta_{max}, t) \quad (4)$$

where d is the MRT factor at $\theta_{max}$, and t is time. For example, according to an embodiment, the controller 116 may assign a value to each pixel or voxel based on the value MRT($\theta_{max}$) for that particular pixel or voxel. Pixels or voxels that represent a coherent reflector will have a relatively high MRT at $\theta_{max}$. In contrast, pixels or voxels that represent a diffuse reflector, such as soft tissue or fluid, will have a relatively low MRT at $\theta_{max}$. Using the MRT at $\theta_{max}$ to determine pixel or voxel values when generating an image will result in an image that weights the coherent reflector more strongly than the non-specular portions of the image.

Figure 11:
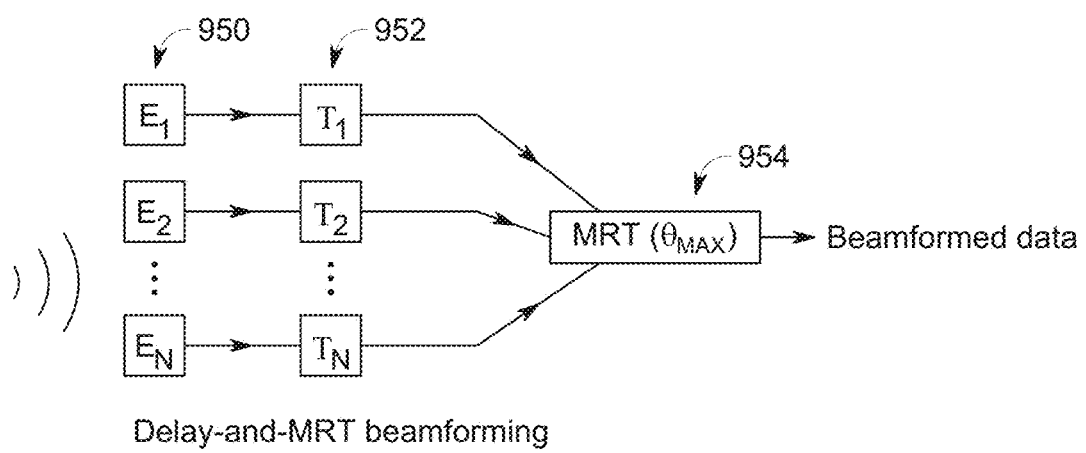
FIG. 11 is schematic representation of a delay-and-MRT beamforming technique in accordance with an exemplary embodiment

FIG. 11 shows a schematic representation of using values from the MRT in place of delay-and-sum beamforming in accordance with an exemplary embodiment. FIG. 11 includes a first column 950 representing elements $E_1, E_2, \ldots, E_N$. FIG. 11 includes a second column 952 representing the delays applied to the data from each of the respective elements. The delays are represented as $T_1, T_2, \ldots, T_N$. After the delays have been applied to the data from the elements, at 954 the controller 116 calculates the MRT at $\theta_{max}$ based on the data with the delays applied. For purposes of this disclosure, the technique schematically illustrated in FIG. 11 will be referred to as delay-and-MRT beamforming.

Figure 12:
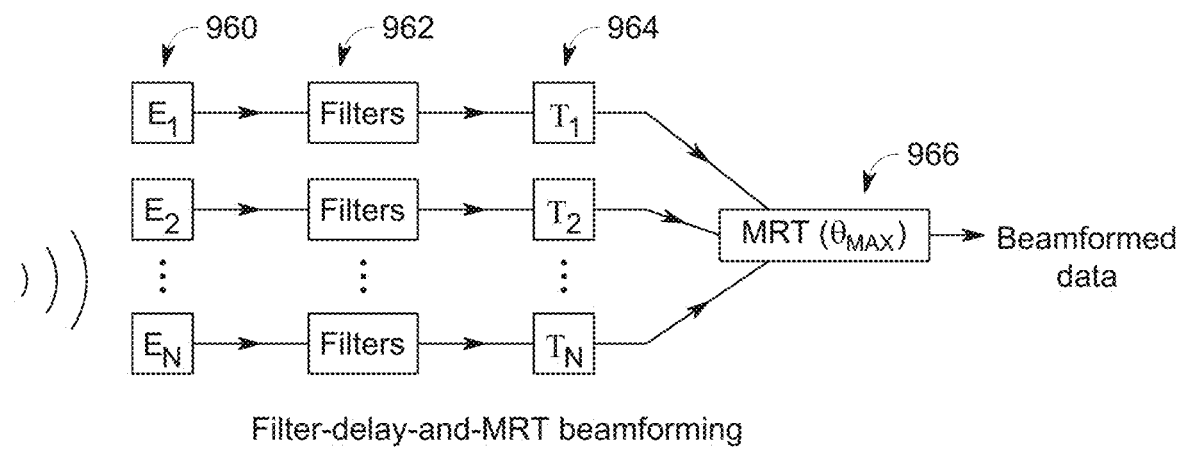
FIG. 12 is a schematic representation of a filter-delay-and-MRT beamforming technique in accordance with an exemplary embodiment.

FIG. 12 shows a schematic representation of using values from the MRT in place of delay-and-sum beamforming in accordance with an exemplary embodiment. FIG. 12 includes a first column 960 representing elements $E_1$, $E_2$, ..., $E_N$. FIG. 11 includes a second column 962 representing filters that filter the data from each of the elements. FIG. 11 includes a third column 964 representing the delays applied to the data from each of the respective elements. The delays are represented as $T_1$, $T_2$, ..., $T_N$. After the delays have been applied to the data from the elements, the controller 116 calculates the MRT at $\theta_{max}$ based on the filtered data with the delays applied. For purposes of this disclosure, the technique schematically illustrated in FIG. 12 will be referred to as delay-filtered-and-MRT beamforming.

Figure 13:
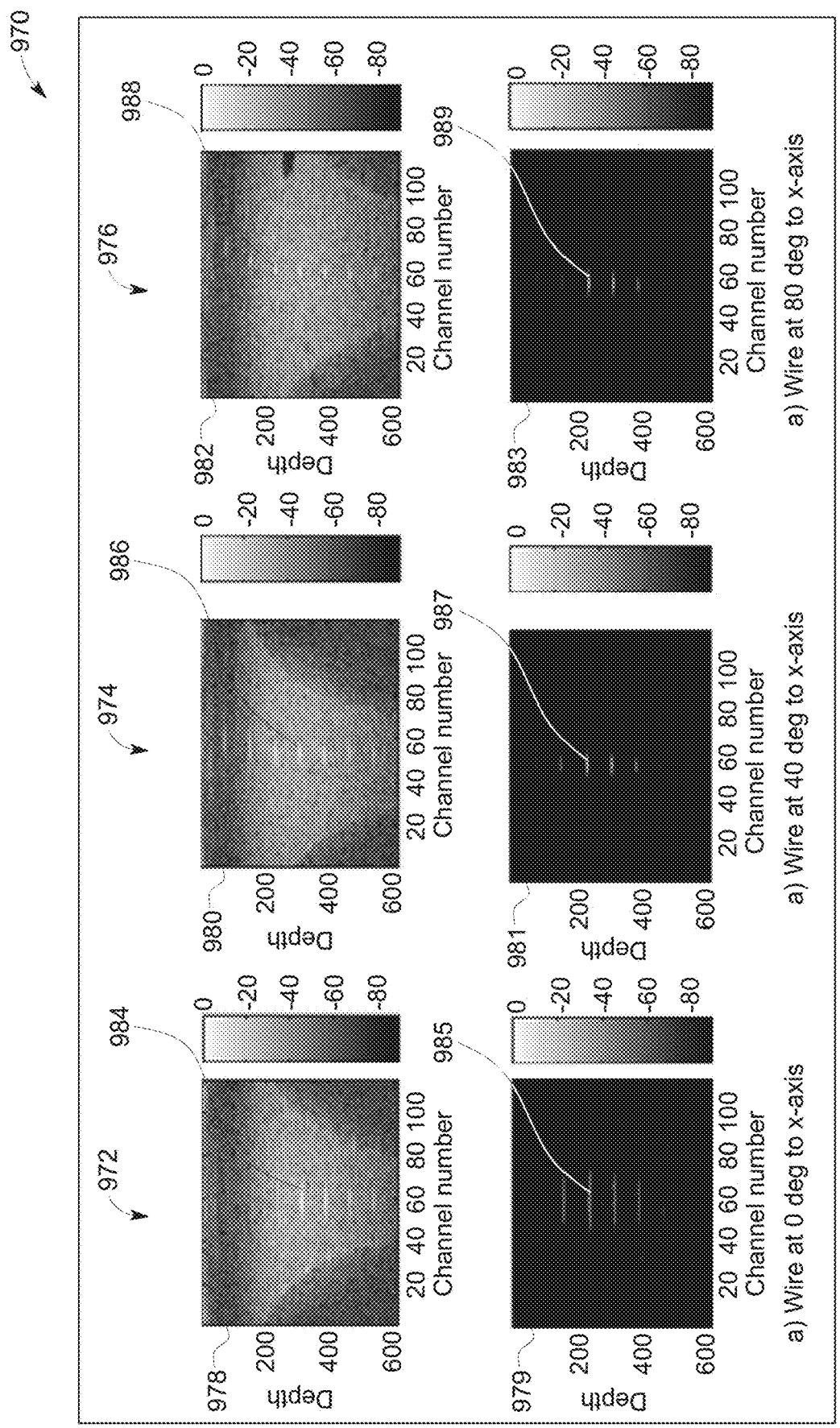
FIG. 13 is a representation of a comparison between images generated using delay-and-sum beamforming and images generated using delay-and-MRT beamforming in accordance with an exemplary embodiment.

FIG. 13 is a table 970 showing a comparison between images generated using a conventional delay-and-sum beamforming and images generated from a delay-and-MRT beamforming according to an exemplary embodiment. The table 970 shows the results of different beamforming techniques applied to the same data. For example, a first column 972 shows the results from ultrasound channel data acquired with the coherent reflector at 0 degrees with respect to the x-axis on the 2D aperture. A second column 974 shows the results from a ultrasound channel data acquired with the coherent reflector at an angle of 40 degrees with respect to the x-axis on the 2D aperture. And a third column 976 shows the results from ultrasound channel data acquire with the coherent reflector at an angle of 80 degrees with respect to the x-axis on the 2D aperture. The table 970 includes a first b-mode image 978, a first MRT b-mode image 979, a second B-mode image 980, a second MRT b-mode image 981, a third b-mode image 982, and a third MRT b-mode image 983. The b-mode images, namely the first b-mode image 978, the second b-mode image 980, and the third b-mode image 982 were each generated using a traditional delay-and-sum beamforming approach. The MRT b-mode images, i.e., the first MRT b-mode image 979, the second MRT b-mode image 981, and the third MRT b-mode image 983 were each beamformed using the delay-and-MRT beamforming described with respect to FIG. 11.

A line 984 represents the coherent reflector in the first b-mode image 978, while a line 985 represents the coherent reflector in the first MRT b-mode image 979. A line 986 represents the coherent reflector in the second b-mode image 980, while a line 987 represents the coherent reflector in the second MRT b-mode image 981. A line 988 represents the coherent reflector in the third b-mode image 982, while a line 989 represents the coherent reflector in the third MRT b-mode image 983. It is qualitatively apparent that the contrast ratio between the coherent reflectors and the rest of the image is much higher for the images that were beamformed using the delay-and-MRT technique compared to the images that were beamformed using the conventional delay-and-sum beamforming technique.

The contrast ratio was calculated on the ultrasound channel data using the following equation:

$$CR = 20 * \log 10\left(\frac{I_{specular}}{I_{surrounding}}\right) \quad (5)$$

where CR is the contrast ratio, $I_{specular}$ is the intensity of the portion of the image representing the coherent reflector and $I_{surrounding}$ is the intensity of the non-specular portions of the image (i.e., all the portions of the image other than the coherent reflector). The contrast ratios of an image beamformed using the delay-and-MRT beamforming technique discussed above was found to be approximately 4 times the contrast ratios of an image beamformed using the conventional delay-and-sum technique on the same ultrasound channel data. Table 1 shows the experimental results of the contrast ratios obtained using three different beamforming techniques: conventional b-mode (delay-and-sum), delay-and variance, and MRT b-mode (i.e., delay-and-MRT beamforming). The contrast ratios were obtained on a Vivid E95.

TABLE 1

|  | Orientation of needle/catheter (approximate ground truth)-α | | |
| --- | --- | --- | --- |
|  | α = 0° | α = 40° | α = 80° |
| Conventional B-mode | −23 dB | −31 dB | −26 dB |
| Delay and Variance | −42 dB | −58 dB | −57 dB |
| MRT B-mode | −96 dB | −127 dB | −101 dB |

Referring back to FIG. 2, at 218, the controller 116 determines if the coherent reflector 302 should be tracked. If the coherent reflector 302 should not be tracked, then the method ends at 219. If the coherent reflector should be tracked, then the method 200 advances to step 220. At step 220, the controller controls the transmit beamformer 101, the transmitter 102, the probe 106, the receiver 108 and the processor 110 to acquire 2D ultrasound data including the coherent reflector 302. The controller 116 may cause the transmit beamformer 101 to control the position of the plane or frame from which the 2D ultrasound data is acquired to include the coherent reflector 302. For example, according to a first embodiment, the controller 116 may control the plane to include a straight portion of the coherent reflector 302. In other words, the plane of the 2D ultrasound acquisition may be positioned so that the coherent reflector 302, or at least the straight portion of the coherent reflector 302, is within the plane. According to other embodiments, the controller 116 may steer the frames to acquire 3D data including the coherent reflector.

Figure 14:
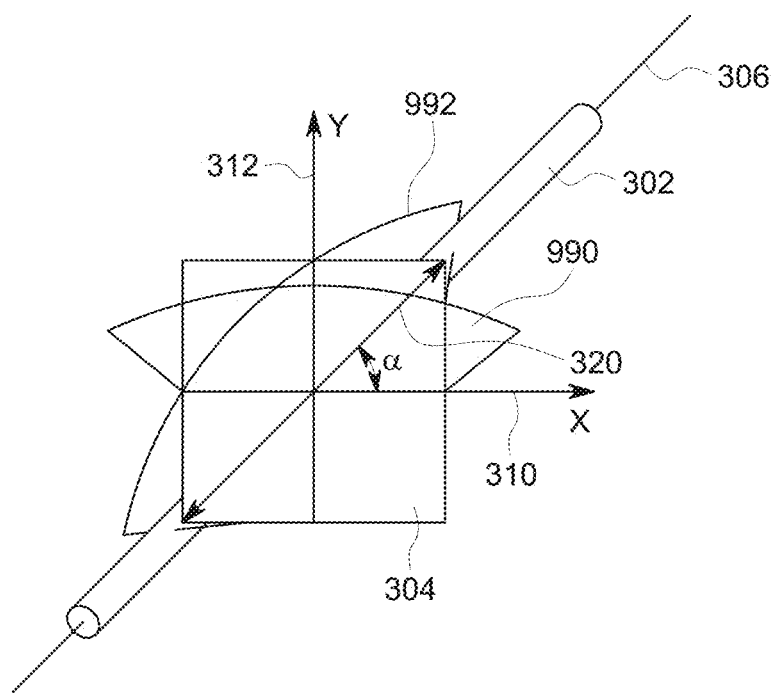
FIG. 14 is a schematic representation showing how a frame may be steered according to an exemplary embodiment.

FIG. 14 is a schematic representation of illustrating how the controller 116 may beam steer in order to acquire ultrasound channel data including the coherent reflector 302. FIG. 14 includes the 2D aperture 304, the coherent reflector 302, the longitudinal axis 306, the x-axis 310, the y-axis 312, the first angle α, a first 2D frame 990, and a second 2D frame 992. According to an embodiment, the ultrasound imaging system 100 may initially acquire ultrasound data representing the first 2D frame 990. However, after determining the position and orientation of the coherent reflector 302 at step 211 of the method 200, the controller 116 may use the position and orientation information to steer the 2D frame so it includes the coherent reflector 302 with the longitudinal axis 306 lying inside the second 2D frame 992. For example, the second frame 992 is an example of a 2D frame that has been steered to include the coherent reflector 302. The second 2D frame 992 is oriented so that it passes through the coherent reflector 302 along the longitudinal axis 306. While steps 220 was described according to an embodiment where the data was 2D data, according to other embodiments, the controller 116 may acquire 3D data including the coherent reflector 302 based on the position and orientation of the coherent reflector 302. According to an embodiment, the steps 202, 204, 206, 208, 210, 211, 213, 216, 218, 220, and 222 may be iteratively repeated multiple times as the coherent reflector 302 is moved. For example, if the coherent reflector is an interventional device, like a biopsy needle, an operator may adjust the position and orientation of the biopsy needle in order target the desired structure in a patient's body. By iteratively repeating steps 202, 204, 206, 208, 210, 211, 213, 216, 218, 220, and 222 the method 200 adjusts the position of the 2D frame so that it tracks the position of the coherent reflector 302 as it moves. Acquiring 2D frames of the coherent reflector 302 allows for high spatial and temporal resolution, which may aid the clinician in accurately positioning the coherent reflector 302. For embodiments where the data acquired at step 220 is 3D data, the volume-of-interest may be smaller than the volume-of-interest acquired at step 202 in order to provide improvements in spatial and/or temporal resolution. This provides the clinician with a live image showing the position of the coherent reflector 302 with respect to the patient's anatomy as the coherent reflector is repositioned in the patient's body. The clinician may use this information to more accurate perform the desired interventional procedure. According to other embodiments, the method 200 may be modified to omit some of the steps that were previously described. For example, some embodiments may not include steps 220 and 222. They may instead enhance the coherent reflector 302 at step 213 and display the image with the enhanced coherent reflector. Other embodiments may omit steps 213 and 216. They may instead use the information about the position and orientation of the coherent reflector 302 to perform steps 220 and 222. These embodiments would provide the clinician with a real-time image showing the position of the coherent reflector 302. Still other embodiments may omit step 216. The controller 116 may use the position and orientation information determined at step 211 in order to control the acquisition of the coherent reflector 302 at step 220. For example, the only images displayed to the user on the display device 118 may displayed at step 222. The images displayed at step 22 may be a 2D image plane of the plane including the coherent reflector 302 or a 2D reformation of the 3D volume acquired to include the coherent reflector 302. The 2D reformation of the 3D volume may be based on either the ultrasound channel data acquired at step 202 or on the smaller volume of data acquired at step 220 according to various embodiments.

According to an embodiment where the method 200 iteratively repeat steps 202, 204, 206, 208, 210, 211, 213, 216, 218, 220, and 222, the controller 116 may use the position and orientation information from step 211 to adjust the acquisition of ultrasound channel data at step 202. For example, the controller 116 may use position and orientation information of the coherent reflector 302 determined at step 211 to acquire a smaller volume-of-interest or region or interest at step 220. This will still capture the coherent reflector 302 and it will enable improvements in one or both of spatial resolution and temporal resolution.

Referring back to step 213, according to another embodiment, the controller 116 may generate a fused image to enhance the coherent reflector. For example, the fused image may be a fusion of a b-mode image generated from a conventional delay-and-sum beamforming technique, like that which was described with respect to FIG. 10 and a beamforming technique using the MRT. For example, the image generated with delay-and-sum beamforming may be fused with an image generated from either delay-and-MRT beamforming (shown in FIG. 11) or filter-delay-and-MRT beamforming (shown in FIG. 12). The fused image would advantageously show surrounding anatomical data from the image generated from delay-and-sum beamforming and improve the contrast of the coherent reflect based on the image generated from either the delay-and-MRT beamforming or the filter-delay-and-MRT beamforming.

Figure 15:
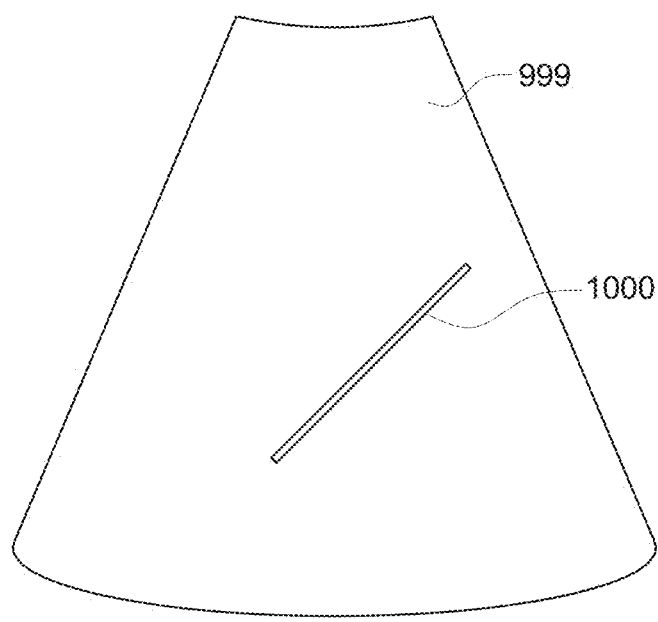
FIG. 15 is a schematic representation of an image including a graphical indicator in accordance with an embodiment.

FIG. 15 is a schematic representation of a displayed image 999 including a graphical indicator 1000 according to an exemplary embodiment. The graphical indicator 1000 serves as an enhanced representation of the coherent reflector. The controller 116 may, for instance, display image 999 at step 216. The graphical indicator 1000 comprises a line, but as described above, the graphical indicator 1000 may comprise and icon or another shape to convey the position and orientation of the coherent reflector according to other embodiments.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method for detecting a coherent reflector with an ultrasound imaging system including a processor, the method comprising:
    acquiring ultrasound channel data from a volume with a probe including a 2D aperture;
    calculating, with the processor, a Modified Radon Transform (MRT) from the ultrasound channel data;
    identifying with the processor a first angle of a projection of the coherent reflector in a plane parallel to the 2D aperture based on the MRT;
    detecting with the processor a line-shaped echo pattern in the ultrasound channel data;
    determining, with the processor, a second angle of the coherent reflector with respect to the 2D aperture based on the position of the line-shaped echo pattern;
    determining, with the processor, a position and an orientation of the coherent reflector based on the first angle and the second angle;
    enhancing a representation of the coherent reflector in an image generated based on the ultrasound channel data; and
    displaying the image on a display device after enhancing the representation of the coherent reflector.

2. The method of claim 1, wherein enhancing the representation of the coherent reflector comprises generating a graphical indicator representing the coherent reflector and displaying the graphical indicator on the image.

3. The method of claim 2, where the graphical indicator comprises a line, an arrow, or a cylinder.

4. The method of claim 1, wherein enhancing the representation of the coherent reflector comprises using the MRT to generate the image.

5. The method of claim 4, wherein using the MRT to generate the image comprises using a delay-and-MRT beamforming.

6. The method of claim 1, wherein enhancing the representation comprises generating a fused image, where the fused image comprises a b-mode image combined with an image generated using a delay-and-MRT beamforming.

7. The method of claim 1, further comprising acquiring additional ultrasound channel data including the coherent reflector based on the position and the orientation of the coherent reflector.

8. The method of claim 7, where the additional ultrasound channel data comprises 2D ultrasound data of a plane including the coherent reflector.

9. The method of claim 7, wherein the additional ultrasound channel data comprises 3D ultrasound data of a second volume including the coherent reflector, where the second volume is smaller than the volume.

10. The method of claim 7, further comprising tracking the coherent reflector in real-time based on the position and the orientation of the coherent reflector.

11. The method of claim 8, further comprising adjusting a position of the plane in real-time to track the coherent reflector based on the position and the orientation of the coherent reflector.

12. An ultrasound imaging system comprising:
a probe including a 2D aperture;
a display device; and
a processor in electronic communication with the probe and the display device,
wherein the processor is configured to:
control the probe to acquire ultrasound channel data from a volume;
calculate a Modified Radon Transform (MRT) from the ultrasound channel data;
identify a first angle of a projection of the coherent reflector on a plane parallel to the 2D aperture based on the MRT;
detect a line-shaped echo pattern in the ultrasound channel data;
determine a second angle of the coherent reflector with respect to the 2D aperture based on the position of the line-shaped echo pattern;
determine a position and an orientation of the coherent reflector based on the first angle and the second angle;
enhance a representation of the coherent reflector in an image generated based on the ultrasound channel data; and
display the image on the display device after enhancing the representation of the coherent reflector.

13. The ultrasound imaging system of claim 12, wherein the processor is configured to enhance the representation of the coherent reflector by generating a graphical indicator representing the coherent reflector and displaying the graphical indicator on the image.

14. The ultrasound imaging system of claim 12, wherein the processor is configured to enhance the representation of the coherent reflector by using the MRT to generate the image.

15. The ultrasound imaging system of claim 14, wherein the processor is configured to use a delay-and-MRT beamforming to generate the image.

16. The ultrasound imaging system of claim 12, wherein the processor is configured to enhance the representation of the coherent reflector by generated a fused image comprising a b-mode image combined with an image generated using a delay-and-MRT beamforming.

17. The ultrasound imaging system of claim 12, wherein the processor is configured to acquire additional ultrasound channel data including the coherent reflector based on the position and the orientation of the coherent reflector.

18. The ultrasound imaging system of claim 17, wherein the processor is further configured to track the position and the orientation of the coherent reflector in real-time.

19. The ultrasound imaging system of claim 18, where the additional ultrasound channel data comprises 2D ultrasound data of a plane including the coherent reflector, and wherein the processor is further configured to adjust a position of the 2D plane in real-time to track the coherent reflector based on the position and the orientation of the coherent reflector.

20. The ultrasound imaging system of claim 18, where the additional ultrasound channel data comprises 3D ultrasound data of a second volume that is smaller than the volume, where the second volume includes the coherent reflector, and wherein the processor is further configured to adjust a position of the second volume in real-time to track the coherent reflector based on the position and orientation of the coherent reflector.

* * * * *